United States Patent [19]

Tsukamoto et al.

[11] Patent Number: 5,763,197
[45] Date of Patent: Jun. 9, 1998

[54] HUMAN HEMATOPOIETIC STEM CELL

[75] Inventors: Ann Tsukamoto, Palo Alto; Charles M. Baum, Mountain View, both of Calif.; Yukoh Aihara, Yokohama, Japan; Irving Weissman, Palo Alto, Calif.

[73] Assignee: Systemix, Inc., Palo Alto, Calif.

[21] Appl. No.: 720,883

[22] Filed: Jun. 25, 1991

Related U.S. Application Data

[63] Continuation-in-part of Ser. No. 502,616, Mar. 30, 1990, Pat. No. 5,061,620.

[51] Int. Cl.⁶ ..................................................... G01N 33/53
[52] U.S. Cl. ........................................ 435/7.21; 435/7.24
[58] Field of Search ..................... 435/7.21, 29, 32, 435/240.2, 240.23, 240.243, 240.1, 7.24; 530/300, 326, 327, 399; 514/2

[56] References Cited

U.S. PATENT DOCUMENTS

| | | | |
|---|---|---|---|
| 4,714,680 | 12/1987 | Civin | 435/240.25 |
| 5,004,681 | 4/1991 | Boyse et al. | 435/2 |
| 5,013,824 | 5/1991 | Abrams et al. | 530/300 |
| 5,032,508 | 7/1991 | Naughton et al. | 435/32 |
| 5,087,570 | 2/1992 | Weissman et al. | 435/240.1 |

*Primary Examiner*—Stephen Walsh
*Attorney, Agent, or Firm*—Pamela J. Sherwood; Fish & Richardson P.C.

[57] ABSTRACT

Human hematopoietic stem cells are provided by separation of the stem cells from dedicated cells. The stem cells may than be maintained by regeneration in an appropriate growth medium. Means are provided for assaying for the stem cells as to their capability for producing members of each of the hematopoietic lineages.

2 Claims, No Drawings

HUMAN HEMATOPOIETIC STEM CELL

CROSS-REFERENCE TO RELATED APPLICATION

This application is a continuation-in-part of application Ser. No. 502,616, filed Mar. 30, 1990 now U.S. Pat. No. 5,061,620.

INTRODUCTION

1. Technical Field

The field of this invention is the isolation, regeneration and use of hematopoietic stem cells.

2. Background

Mammalian blood cells provide for an extraordinarily diverse range of activities. The blood cells are divided into several lineages, including lymphoid, myeloid and erythroid. The lymphoid lineage, comprising B-cells and T-cells, provides for the production of antibodies, regulation of the cellular immune system, detection of foreign agents in the blood, detection of cells foreign to the host, and the like. The myeloid lineage, which includes monocytes, granulocytes, megakaryocytes as well as other cells, monitors for the presence of foreign bodies in the blood stream, provides protection against neoplastic cells, scavenges foreign materials in the blood stream, produces platelets, and the like. The erythroid lineage provides the red blood cells, which act as oxygen carriers.

Despite the diversity of the nature, morphology, characteristics and function of the blood cells, it is presently believed that there is a single progenitor, which is capable of self regeneration and by exposure to growth factors becomes dedicated to a specific lineage.

The stem cell population constitutes only a small percentage of the total number of leukocytes in bone marrow. In addition, at the present time it is not known how many of the markers associated with differentiated cells are also present on the stem cell. One marker which is reported to provide for some enrichment of progenitor activity is Class II HLA (particularly a conserved DR epitope recognized by a monoclonal antibody designated J1-43). However, these markers are found on numerous lineage committed hematopoietic cells. One marker which has been indicated as present on stem cells, CD34, is also found on a significant number of lineage committed progenitors. In particular, B-cells (CD19+) and myeloid cells (CD33+) make up 80–90% of the CD34+ population. Moreover, a combination of CD3, 8, 10, 15, 19, 20, and 33 will mark >90% of all CD34+ cells. Therefore, in view of the small proportion of the total number of cells in the bone marrow which are stem cells, the uncertainty of the markers associated with the stem cell as distinct from more differentiated cells, and the general inability to biologically assay for human stem cells, the identification and purification of stem cells has been elusive. Recently, the mouse stem cell has been obtained in at least highly concentrated, if not a purified form, where fewer than about 30 cells obtained from bone marrow were able to reconstitute all of the lineages of the hematopoietic system of a lethally irradiated mouse. Indeed, one injected cell should be able to reconstitute all of the hematopoietic lineages.

The Thy-1 molecule is a highly conserved protein present in the brain and hematopoietic system of rat, mouse and man. These species differentially express this antigen and the true function of this molecule is unknown. However, the Thy-1 molecule has been identified on rat and mouse hematopoietic stem cells. This protein is also present on human bone marrow cells and is useful for the selection of hematopoietic stem cells.

There is a strong interest in identifying the human hematopoietic stem cell. Having possession of the stem cell will allow for identification of growth factors associated with its self regeneration. In addition, there may be as yet undiscovered growth factors associated (1) with the early steps of dedication of the stem cell to a particular lineage; (2) the prevention of such dedication; and (3) the negative control of stem cell proliferation. The availability of stem cells would be extremely useful in bone marrow transplantation, as well as transplantation of other organs in association with the transplantation of bone marrow. Stem cells are important targets for gene therapy, where the inserted genes promote the health of the individual into whom the stem cells are transplanted. In addition, the ability to isolate the stem cell may serve in the treatment of lymphomas and leukemias, as well as other neoplastic conditions, e.g., breast cancer. Thus, there have been worldwide efforts toward isolating the human hematopoietic stem cell in substantially pure or pure form.

RELEVANT LITERATURE

U.S. Pat. No. 4,714,680 describes a composition comprising human stem cells. EPA 89.304651.6 describes the isolation of mouse stem cells. See also the references cited therein. Analysis for hematopoietic progenitors have been reported by Whitlock and Witte, *PNAS USA* (1982) 79:3608; and Whitlock et al., *Cell* (1987) 48:1009. Thy-1 is a surface marker of reconstituting rodent bone marrow stem cells (Berman and Baush Exp. *Hematol.* (1985) 13:1952 and Goldschneider et al., J. *Exp. Med.* (1978) 148:1351). Müller-Sieburg et al., *Cell* (1986) 44:653 describe Thy-1$^{lo}$ Lin$^-$ mouse hematopoietic stem cells and the use of limit dilution.

SUMMARY OF THE INVENTION

Methods resulting in the isolation of substantially homogenous compositions of human hematopoietic stem cells are provided. The methods employ a predetermined separation regimen and bioassays for establishing the generation of each of the hematopoietic lineages from the isolated cells. The human stem cells find use: (1) in regenerating the hematopoietic system of a host deficient in stem cells, (2) in a host that is diseased and can be treated by removal of bone marrow, isolation of stem cells and treatment of individuals with drugs or irradiation prior to re-engraftment of stem cells, (3) producing various hematopoietic cells, (4) detecting and evaluating growth factors relevant to stem cell self-regeneration; (5) the development of hematopoietic cell lineages and assaying for factors associated with hematopoietic development; and (6) treatment of genetic diseases through gene replacement in autologous stem cells.

DESCRIPTION OF THE SPECIFIC EMBODIMENTS

A human stem cell composition is provided, substantially free of cells dedicated to a particular lineage, cells carrying markers associated with lineage dedication, wherein the stem cells are able to regenerate and differentiate to populate the various hematopoietic lineages. The substantially homogenous composition may be obtained by selective isolation of cells free of markers associated with differentiated cells, while displaying epitopic characteristics associated with the stem cells, and by regeneration of the isolated stem cells in defined culture systems leading to different hematopoietic cell lineages.

The stem cells are characterized by both the presence of markers associated with specific epitopic sites identified by antibodies and the absence of certain markers as identified by the lack of binding of certain antibodies. It is not necessary that selection is achieved with a marker specific for stem cells. By using a combination of negative selection (removal of cells) and positive selection (isolation of cells), a substantially homogeneous stem cell composition can be achieved.

If desired, a large proportion of differentiated cells may be removed by initially using a "relatively crude" separation. The source of the cells may be the bone marrow, fetal, neonate or adult or other hematopoietic cell source, e.g., fetal liver, peripheral blood, umbilical cord blood, and the like. For example, magnetic bead separations may be used initially to remove large numbers of lineage committed cells, namely major cell populations of the hematopoietic systems, including such lineages as T-cells, B-cells, (both pre-B and B-cells), myelomonocytic cells, or minor cell populations, such as megakaryocytes, mast cells, eosinophils and basophils. Desirably, at least about 70%, usually at least 80% of the total hematopoietic cells will be removed. It is not essential to remove every dedicated cell class, particularly the minor population members at the initial stage. Usually, the platelets and erythrocytes will be removed prior to sorting. Since there will be positive selection in the protocol, the dedicated cells lacking the positively selected marker will be left behind. However, it is preferable that there be negative selection for all of the dedicated cell lineages, so that in the final positive selection, the number of dedicated cells present is minimized.

The stem cells are characterized by being for the most part $CD34^+$, $CD3^-$, $CD7^-$, $CD8^-$, $CD10^-$, $CD14^-$, $CD15^-$, $CD19^-$, $CD20^-$, $CD33^-$, and $Thy-1^+$. A highly stem cell concentrated cell composition is $CD34^+$, $CD10^-$, $CD19^-$ and $CD33^-$, more particularly in addition $CD3^-$ and $CD8^-$, preferably in addition $Thy-1^+$. The $CD3^-$, $8^-$, $10^-$, $19^-$, $20^-$ and $33^-$ will be referred to as $Lin^-$. The CD10/19/20 markers are associated with B-cells, CD3/4/8 markers are associated with T-cells, CD14/15/33 cell markers are associated with myeloid cells. The Thy-1 marker is absent on human T-cells. Also, for human $CD34^+$, rhodamine 123 can divide the cells into high and low subsets. See Spangrude, (1990) Proc. Natl. Acad. Sci. 87, 7433 for a description of the use of rhodamine 123 with mouse stem cells. Preferably the cells are rhodamine low.

In order to obtain the subject stem cells, it is necessary to isolate the rare pluripotent human stem cell from the other cells in bone marrow or other hematopoietic source. Initially, bone marrow cells may be obtained from a source of bone marrow, e.g., iliac crests, tibiae, femora, spine, or other bone cavities. Other sources of human hematopoietic stem cells include embryonic yolk sac, fetal liver, fetal and adult spleen, blood, including adult peripheral blood and umbilical cord blood.

For isolation of bone marrow from fetal bone or other bone source, an appropriate solution may be used to flush the bone, which solution will be a balanced salt solution, conveniently supplemented with fetal calf serum or other naturally occurring factors, in conjunction with an acceptable buffer at low concentration, generally from about 5–25 mM. Convenient buffers include Hepes, phosphate buffers, lactate buffers, etc. Otherwise bone marrow may be aspirated from the bone in accordance with conventional ways.

Morphologic evaluation of the 34+Thy+Lin– cells indicates that the multipotent progenitors, "stem cells" are of medium size. Light scatter evaluation shows that "stem cells" have a blast cell profile with low side scatter. These observations indicate that the "stem cells" have a unique density profile. It has been found that the low density fractions from density fractionated human bone marrow are enriched for CD34+Thy+Lin– cells.

Various techniques may be employed to separate the cells by initially removing cells of dedicated lineage. Monoclonal antibodies are particularly useful for identifying markers (surface membrane proteins) associated with particular cell lineages and/or stages of differentiation. The antibodies may be attached to a solid support to allow for crude separation. The separation techniques employed should maximize the retention of viability of the fraction to be collected. For "relatively crude" separations, that is, separations where up to 10%, usually not more than about 5%, preferably not more than about 1%, of the total cells present having the marker, may remain with the cell population to be retained, various techniques of different efficacy may be employed. The particular technique employed will depend upon efficiency of separation, cytotoxicity of the methodology, ease and speed of performance, and necessity for sophisticated equipment and/or technical skill.

Procedures for separation may include magnetic separation, using antibody-coated magnetic beads, affinity chromatography, cytotoxic agents joined to a monoclonal antibody or used in conjunction with a monoclonal antibody, e.g., complement and cytotoxins, and "panning" with antibody attached to a solid matrix, e.g., plate, or other convenient technique. Techniques providing accurate separation include fluorescence activated cell sorters, which can have varying degrees of sophistication, e.g., a plurality of color channels, low angle and obtuse light: scattering detecting channels, impedance channels, etc.

One procedure which may be used is in a first stage after incubating the cells from the bone marrow for a short period of time at reduced temperatures, generally about 4° C., with saturating levels of antibodies specific for a particular cell type, e.g., CD3 and 8 for T-cell determinants, the cells may then be washed with a fetal calf serum (FCS) cushion. The cells may then be suspended in a buffer medium as described above and separated by means of the antibodies for the particular determinants, using various proteins specific for the antibodies or antibody-antigen complex.

Conveniently, the antibodies may be conjugated with markers, such as magnetic beads, which allow for direct separation, biotin, which can be removed with avidin or streptavidin bound to a support, fluorochromes, which can be used with a fluorescence activated cell sorter, or the like, to allow for ease of separation of the particular cell type. Any technique may be employed which is not unduly detrimental to the viability of the remaining cells.

Conveniently, after substantial enrichment of the cells lacking the mature cell markers, generally by at least about 50%, preferably at least about 70%, the cells may now be separated by a fluorescence activated cell sorter (FACS) or other methodology having high specificity. Multi-color analyses may be employed with the FACS which is particularly convenient. The cells may be separated on the basis of the level of staining for the particular antigens. In a first separation, starting with at least about $1 \times 10^{10}$, preferably at least about $3 \times 10^{10}$ cells, the antibody for CD34 may be labeled with one fluorochrome, while the antibodies for the various dedicated lineages may be conjugated to a different fluorochrome. Fluorochromes which may find use in a multi-color analysis include phycobiliproteins, e.g., phycoerythrin and allophycocyanins, fluorescein, Texas red, etc. While each of the lineages may be separated in a separate step, desirably the lineages are separated at the same time as one is positively selecting for CD34 or equivalent marker. Generally, the number of cells obtained will be fewer than about 1% of the original cells, generally fewer than about 0.5% and may be as low as 0.2% or less.

The cells may then be further separated by positively selecting for Thy$^+$, where the cells will generally be fewer than 0.5% of the original cells, generally in the range of 0.01–0.5%. The cells may be selected against dead cells, by employing dyes associated with dead cells (propidium iodide, LDS). Desirably, the cells are collected in a medium comprising 2% fetal calf serum. Other techniques for positive selection may be employed, which permit accurate separation, such as affinity columns, and the like. The method should permit the removal to a residual amount of less than about 20%, preferably less than about 5%, of the non-stem cell populations.

The CD34$^+$Lin$^-$ and the CD34$^+$Lin$^-$Thy-1$^+$ have low side scatter and low forward scatter profiles by FACS analysis. Cytospin preparations show the stem cell to have a size between mature lymphoid cells and mature granulocytes. Cells may be selected based on light-scatter properties as well as their expression of various cell surface antigens.

While it is believed that the particular order of separation is not critical to this invention, the order indicated is preferred. Preferably, cells are initially separated by a coarse separation, followed by a fine separation, with positive selection of a marker associated with stem cells and negative selection for markers associated with lineage committed cells. This separation is followed by selection for a cellular composition having multi-lineage potential and enhanced self-regeneration capability.

Compositions having greater than 90%, usually greater than about 95% of human stem cells may be achieved in this manner, where the desired stem cells are identified by being CD34$^+$, Lin$^-$ and Thy-1$^+$ and being able to provide for cell regeneration and development of members of all of the various hematopoietic lineages. Ultimately, a single cell could be obtained from a stem cell composition and be used for long term reconstitution of an immunodeficient human, if one could be assured that the cell was located in the proper environment in vivo.

The subject compositions are found to provide for production of myeloid cells and lymphoid cells in appropriate cultures, cultures providing hydrocortisone for production of myeloid cells (associated with Dexter-type cultures) and B lymphocytes in cultures lacking hydrocortisone, (associated with Whitlock-Witte type cultures). In each of the cultures, mouse or human stromal cells are provided, which may come from various strains, AC3 or AC6, stromal cells derived from mouse or human fetal bone marrow by selection for the ability to maintain human stem cells, and the like. The medium employed for the culturing of the cells is conveniently a defined enriched medium, such as IMDM (Iscove fs Modified Dulbecco's Medium), a 50:50 mixture of IMDM and RPMI, and will generally be composed of salts, amino acids, vitamins, $5\times10^{-5}$M 2-ME, streptomycin/penicillin and 10% fetal calf serum, and may be changed from time to time, generally at least about once to twice per week. Particularly, by transferring cells from one culture with hydrocortisone, to the other culture without hydrocortisone, and demonstrating the production of members of the different lineages in the different cultures, the presence of the stem cell and its maintenance is supported. In this manner, one may identify the production of both myeloid cells and B-cells.

To demonstrate differentiation to T-cells, one may isolate fetal thymus and culture the thymus for from 4–7 days at about 25° C., so as to substantially deplete the lymphoid population of the fetal thymus. The cells to be tested are then microinjected into the thymus tissue, where the HLA of the population which is injected is mismatched with the HLA of the thymus cells. The thymus tissue may than be transplanted into a scid/scid mouse as described in EPA 0 322 240, particularly transplanting in the kidney capsule.

For red blood cells, one may use conventional techniques to identify BFU-E units, for example methylcellulose culture (Metcalf (1977) In: Recent Results in Cancer Research 61. Springer-Verlag, Berlin, pp 1–227) demonstrating that the cells are capable of developing the erythroid lineage.

In identifying myeloid and B-cell capability, conveniently, the population to be tested is introduced first into a hydrocortisone containing culture and allowed to grow for six weeks in such culture. The medium employed will comprise a 50:50 mixture of RPMI 1640 and IMDM containing 10% FCS, 10% horse serum, streptomycin/penicillin, glutamine and $5\times10^{-7}$M hydrocortisone. During the six week period, it would be anticipated that in the absence of progenitor cells, all of the mature cells would die. If at the end of six weeks, myeloid cells are still observed, one may conclude that there is a progenitor cell which is providing for the continuous differentiation to myeloid cells. At this time, one may then change the medium, so that the medium now lacks hydrocortisone, to encourage the growth of B-cells. By waiting 3–4 weeks and demonstrating the presence of B-cells by FACS analysis, one may conclude that the progenitor cells which previously were capable of producing myeloid cells are also capable of producing B-cells. Human hematopoietic cells grown in the presence of hydrocortisone can be maintained for at least four months. Similarly, human hematopoietic cells grown in the absence of hydrocortisone contain B lymphocytes (CD19$^+$), as well as myelomonocytic cells for at least four months. From these cultures, one may sort for CD34+Lin$^-$, CD34+Thy+, Thy+Lin$^-$, or CD34+Thy+Lin$^-$, which should provide a composition substantially concentrated in the progenitor hematopoietic stem cell. The CD34+Lin$^-$, CD34+Thy+, Thy+Lin$^-$, or CD34+Thy+Lin$^-$ cells obtained from these cultures can give rise to B-cells, T-cells and myelomonocytic cells in the assays described above.

A pluripotent human stem cell may be defined as follows: (1) gives rise to progeny in all defined hematolymphoid lineages; and (2) limiting numbers of cells are capable of fully reconstituting a seriously immunocompromised human host in all blood cell types and their progenitors, including the pluripotent hematopoietic stem cell by cell renewal. In the subject compositions, fewer than a total of about 10$^7$ cells, usually fewer than 10$^6$ cells, may be used to reconstitute an immunocompromised human host, as compared to the number of stem cells included in whole bone marrow transplants ($\sim$10$^7$). The number of cells is required to insure that appropriate seeding at an appropriate site occurs, where the stem cell may self-renew. The number of cells required which become seeded at a proper site for self-renewal may be fewer than 50 cells, and as few as about a total of 20 cells or fewer, are able to fulfill the conditions indicated above. Thus, based on the standards set for the earliest progenitor pluripotent stem cell, the subject compositions are capable of fulfilling these requirements. Furthermore, the subject cells based on analysis of bone marrow cells appear to be in a range of from about 0.01–0.1% of bone marrow cells, particularly 0.01–0.05%.

Once stem cells have been isolated, they may be propagated by growing in conditioned medium from stromal cells, such as stromal cells that can be obtained from bone marrow, fetal thymus or fetal liver, and are shown to provide for the secretion of growth factors associated with stem cell maintenance, coculturing with such stromal cells, or in medium comprising maintenance factors supporting the proliferation of stem cells, where the stromal cells may be allogeneic or xenogeneic. Before using in the coculture, the mixed stromal cell preparations may be freed of hematopoietic cells employing appropriate monoclonal antibodies for removal of the undesired cells, e.g., with antibody-toxin conjugates, antibody and complement, etc. Alternatively, cloned stromal cell lines may be used where the stromal lines may be allogeneic or xenogeneic.

The subject cell compositions may find use in a variety of ways. Since the cells are naive, they can be used to reconstitute fully an irradiated host and/or a host subject to chemotherapy; or as a source of cells for specific lineages, by providing for their maturation, proliferation and differentiation into one or more selected lineages by employing a variety of factors, such as erythropoietin, colony stimulating factors, e.g., GM-CSF, G-CSF, or M-CSF, interleukins, e.g., IL-1, -2, -3, -4, -5, -6, -7, -8, etc., Leukemia Inhibitory Factory (LIF), Steel Factor (St1), or the like, or stromal cells associated with the stem cells becoming committed to a particular lineage, or with their proliferation, maturation and differentiation. The stem cells may also be used in the isolation and evaluation of factors associated with the differentiation and maturation of hematopoietic cells. Thus, the stem cells may be used in assays to determine the activity of media, such as conditioned media, evaluate fluids for cell growth activity, involvement with dedication of particular lineages, or the like.

The stem cells may be used for the treatment of genetic diseases. Genetic diseases associated with hematopoietic cells may be treated by genetic modification of autologous or allogeneic stem cells to correct the genetic defect. For example, diseases such as B-thalassemia, sickle cell anemia, adenosine deaminase deficiency, recombinase deficiency, recombinase regulatory gene deficiency, etc. may be corrected by introduction of a wild-type gene into the stem cells, either by homologous or random recombination. With allogeneic stem cells, normal cells lacking the genetic defect can be used as a therapy. Other indications of gene therapy are introduction of drug resistance genes to enable normal stem cells to have an advantage and be subject to selective pressure, e.g. the multiple drug resistance gene (MDR). Diseases other than those associated with hematopoietic cells may also be treated, where the disease is related to the lack of a particular secreted product such as a hormone, enzyme, interferon, factor, or the like. By employing an appropriate regulatory initiation region, inducible production of the deficient protein may be achieved, so that production of the protein will parallel natural production, even though production will be in a different cell type from the cell type that normally produces such protein. It is also possible to insert a ribozyme, antisense or other message to inhibit particular gene products or susceptibility to diseases, particularly hematolymphotropic diseases.

Alternatively, one may wish to remove a particular variable region of a T-cell receptor from the T-cell repertoire. By employing homologous recombination, or antisense or ribozyme sequence which prevents expression, the expression of the particular T-cell receptor may be inhibited. For hematotropic pathogens, such as HIV, HTLV-I and II, etc. the stem cells could be genetically modified to introduce an antisense sequence or ribozyme which would prevent the proliferation of the pathogen in the stem cell or cells differentiated from the stem cells.

Methods for recombination in mammalian cells may be found in Molecular Cloning, A Laboratory Manual (1989) Sambrook, Fritsch and Maniatis, Cold Spring Harbor, N.Y.

The cells may be frozen at liquid nitrogen temperatures and stored for long periods of time, being thawed and capable of being reused. The cells will usually be stored in 10% DMSO, 70% autologous plasma (irradiated with 2500 rad), 20% Tc199 (Tissue culture medium). Cells are frozen in a programmable cell freezer to $-180°$ C. in liquid nitrogen. Once thawed, the cells may be expanded by use of growth factors or stromal cells associated with stem cell proliferation and differentiation.

The hematopoietic stem cells, either autologous or allogeneic, may be used for treatment of various diseases where toxic therapies may be involved. For example, in the treatment of neoplasia, bone marrow may be removed from the patient (autologous) or from a "matched" donor ("allogeneic") and the stem cells isolated and optimally frozen. The patient's bone marrow may be partially or wholly ablated using irradiation and/or chemotherapy. Once the treatment is completed, the stem cells may be thawed, if appropriate, administered to the patient by any convenient means, e.g., intravascularly, in a physiologically acceptable medium. The patient may then be monitored for signs of engraftment.

The stem cells may be grown in culture, whereby the stem cells may be expanded. In this way, one can repetitively administer stem cells during a course of a toxic therapy.

The following examples are offered by way of illustration and not by way of limitation.

EXPERIMENTAL

Materials and Methods

Antibodies. The antibodies to the various markers were obtained as follows: CD3, 8, 10, 14, 15, 19, 20, 33, 34 (Becton-Dickinson) CD33 (Coulter Immunology), (Dalchau and Fabre, J. Exp. Med. (1979) 149:576). The CD34 antibody (IgG3) Tük3 obtained from A. Ziegler (in Leukocyte Typing IV; White cell differentiation antigens 1989, 817). The CD3, -8, -10, -14, -15, -19, -20, -33 were purchased as FITC conjugates. The antibody from Ziegler was detected using the appropriate anti-IgG3 conjugated to fluorescein (FL), or phycoerythrin (PE) or Texas red (TR) (Caltag). The Thy-1 antibody was a fluorescein, phycoerythrin or biotin conjugate, where the biotin conjugate was detected with TR, FL or PE-avidin (Caltag).

Fluorescence Activated Cell Sorter (FACS) Analysis and Sorting.

A Becton-Dickinson FACS modified as described (Parks and Herzenberg, Meth. Enzymol. (1984) 108:197) was employed. The dual laser instrument allows four fluorescent parameters and two light scatter parameters to be recorded for each analyzed cell. Residual erythrocytes and dead cells and debris were excluded from analysis by light scattering gating and PI (propidium iodide) staining or by scattering alone in 4-color analyses. Compensation for spatial overlaps of fluorescein and phycoerythrin, and fluorescein and propidium iodide was adjusted electronically as described (Parks and Herzenberg, (1984) supra). Four color stains were performed using several combinations of the same reagents conjugated to different fluorochromes to assure that the results were consistent regardless of the various spatial overlaps of the fluorochromes. In addition, the results of 4-color analyses were calibrated by comparison with data from 2- and 3-color analyses.

For cell sorting, the stained samples were maintained at 4° C. throughout the sorting procedure. Sorted drops were collected in RPMI 1640 containing 10% fetal calf serum (Hazelton Biologics Inc., Lenexa, Kans.). Two color sorts employed phycoerythrin to label CD34 and fluorescein to label LIN cells, with propidium iodide (PI) to label dead cells, with both signals being detected and excluded in a single FACS channel. Three color sorts employed Texas red to label CD34, phycoerythrin to label Lin cells and fluorescein to label Thy-1 cells. Following isolation of a cell population by FACS, the sample was diluted 1:1 in HBSS, centrifuged for 10 minutes at a RCF of 200 and resuspended in 50 or 100 µl of HBSS for hemocytometer counting.

The culture assays were performed as follows:

Various murine stromal cell lines were employed, three of which are described in Whitlock et al., Cell (1987) 48:1009–1021. Confluent stromal cell layers were maintained for up to 3–4 weeks without passage by changing of the tissue culture medium every 5–7 days. To passage, the stromal cell layers were washed 3 times with serum-free medium, then overlaid with 2.5 ml (T-25 flask) of 0.5 mg/ml collagenase-dispase (Boehringer-Mannheim, Indianapolis, Ind.) in serum-free medium. The cultures were allowed to incubate 15–30 minutes at 37° C.; then the cells in the enzyme-containing medium were collected and RPMI-1640 medium with serum added. The stromal cells were suspended by pipetting with a Pasteur pipet, then cultured directly at ⅕th to ¹⁄₅₀th the original cell concentration. In general, confluent stromal layers subcultured at 1:10 reached confluency again after 5–7 days. Subclones were obtained by limiting dilution culture from 30 to 0.3 cells per well. Human stromal cell lines were treated similarly.

Cell suspensions of human fetal bone marrow were prepared from long bones of fetuses from 10–18 week gestation. The bones are split lengthwise and the medullary cavity is scraped with a scalpel blade. The bones are then placed in a 1 mg/ml solution of collagenase/dispase in RPMI-1640. The bones are incubated for 30 minutes at 37° C., after which time the medullary cavity is flushed with media (RPMI-1640 with Pen/Strep, 2-ME and 5% FCS) to remove hematopoietic cells. Alternatively, bone marrow may be flushed from the marrow cavity without collagenase/dispase treatment.

Cell suspensions are prepared from livers of 16–20 week gestation fetuses. The liver is minced and then pipetted to release cells. The cell suspension is then placed on a Ficoll gradient to remove hepatocytes, red blood cells and debris. The hematopoietic cells are then harvested.

Adult bone marrow is obtained from marrow aspirates, which are treated to remove red blood cells before use.

Bulk cultures are obtained by placing the human cells on the previously established confluent layer of mouse or human stromal cell lines. From $3\times10^4$ to $2\times10^5$ cells per ml are placed on the stromal cells in either T-25 flasks or 6 well plates, by addition of 3 ml to each well of a 6 well plate or 5 ml to T-25 flask. A 50:50 mixture of RPMI-1640 and IMDM containing 50 µg/ml penicillin/50 µg/ml streptomycin, 1 mM sodium pyruvate, 2 mM glutamine, $5\times10^{-5}$ 2-mercaptoethanol and 10% fetal calf serum is employed. For Dexter-type conditions, IMDM containing 50 µg/ml penicillin/50 µg/ml streptomycin, 1 mM sodium pyruvate, 2 mM glutamine, 10% fetal calf serum, 20% horse serum and $10^{-6}$M hydrocortisone sodium succinate is employed. Bone marrow cells grown in the Dexter-type medium give rise only to myeloid differentiation. Cultures were established with whole cell populations or cells fractionated by their expression of cell surface antigens (CD34, HLA-DR, Thy-1, Lineage markers).

Limiting dilution cultures were prepared using 96 well plates containing the mouse stromal cells as confluent layers. The human cells were titered into the plates at progressively lower concentrations with at least 24 wells plated at each cell concentration. The plates were then examined to determine the percentage of positive wells at each cell number. The data is then plotted graphically.

AC3 and AC6 Cocultures

Cocultures established with the mouse bone marrow stromal cell lines, AC3 or AC6, have served successfully as feeder layers for human cultures and have inhibited fibroblast overgrowth at low cell densities.

(1) Cell suspensions from more than one hundred human fetal bone marrow, fetal liver, or adult bone marrow samples have been cocultured for up to 20 weeks with continuous production of hematopoietic cells during this time indicating that early human progenitors or stem cells have been established in these cultures.

(2) Cultures show small to medium sized human bone marrow cells attached to the mouse stromal cells and proliferation occurs over the first one to three weeks of culture; thereafter they remain fairly stable.

(3) Cells form loose aggregates consisting of non-adherent and adherent cells overlying stromal cells which in turn overlie small to intermediate sized cells (pseudoemperipolesis). Overall, the appearance of the cultures is similar to mouse long-term cultures.

(4) Cytospin and Fluorescence Activated Cell Sorter (FACS) analyses show maintenance of human hematolymphoid cells. In the absence of hydrocortisone (Whitlock-Witte like conditions), cultures are a mixture of myeloid, monocytoid, and lymphoid lineages by morphology. The majority of cells are myeloid and vary from myeloblasts to mature polymorphonuclear cells. From 15–40% of the cells are mononuclear and many of these cells have a lymphoid morphology.

(5) Approximately 20–40% of the cells stain with the CD15 antibody and 10–50% of the cells stain with the B lineage markers, CD10, CD19, or CD20, indicating a significant number of B-cells. Cells selected from fetal bone marrow for CD19 expression survive for less than three weeks in culture. The presence of $CD10^+$ and $CD19^+$ cells after >4 weeks in culture indicates that early B-cells are arising from committed progenitors. In addition, from 1 to 10% of the cells stain for cytoplasmic µ heavy chain which confirms the presence of pre-B-cells. Significant numbers of cells express CD20 although fewer than 1% express sIg, indicating that few of the early B-cells mature under the indicated culture conditions. Furthermore, cultures initiated after depletion of B-cells (CD10, CD19) by cell sorting show B-cell development within one week of culture initiation.

(6) Cultures initiated in the presence of hydrocortisone (Dexter-like conditions) have no detectable T- or B-cells and have a large percentage of granulocytes and myeloid cells as evidenced by FACS analysis and cytospins. The presence of mitotic figures and the long term maintenance of these cultures indicates the presence of some active progenitor cell. When these hydrocortisone containing cultures are switched to media without hydrocortisone, 2 to 6% CD19 cells can be found within two weeks. This data further substantiates the presence of an active progenitor cell in this coculture system.

Using the above defined co-culture system, a limit dilution assay has been developed which can be used to determine the frequency of colony forming cells in the various cell subpopulations. The frequency is determined by the cell number at which 37% of the wells show no colonies. One representative experiment showed that 1/2000 whole bone marrow cells responded while 1/200 and 1/30,000 cells responded in the CD34+ and CD34− subsets respectively.

In addition, a single cell assay has been developed in which single FACS sorted progenitor cells are placed into individual wells of a 96 well plate containing a mouse or human bone marrow stromal cell feeder layer. Results shown on Table 7 indicate that 1 in 40 CD34+ LIN⁻ (Lin=CD3, 10, 19, 20, 15, 33) or 1 in 80 CD34+ Lin+ cells respond by colony formation (0.5–1% of bone marrow). Analysis of the colonies show that 40% and 25% of the colonies are multipotent as determined by FACS and methylcellulose analysis (B lymphoid, myeloid, erythroid) in the CD34+ Lin− and CD34+ Lin+ populations respectively. Further, CD34+ Thy+ cells (0.1–0.5% of bone marrow) show colony growth in 1 in 20 wells. The majority of the colonies are multipotent (>70%). The CD34+Thy+ cells are the most efficient population in terms of growth after transfer to new stromal layers. In contrast, the CD34+ Thy− cells, which represent >90% of the CD34+ cells, respond poorly in the co-culture assay; 1 in 400 cells form colonies, none of which are multipotent. The Thy+ population can also be subdivided according to expression of mature lineage markers. The Thy+Lin− cell subset (0.1–0.5% of bone marrow) responds well in the single cell assay (1/20) while the Thy+ Lin+ subsets responds poorly (0/800). FACS and methylcellulose assays show that >70% of the colonies derived from Thy+Lin− cells are multipotent. The above data indicates that "stem cells" are present in the subset of cells which express CD34 and Thy-1 but lack expression of lineage markers. Cells with this phenotype represent fewer than 1 in 1000 whole bone marrow cells.

One can determine the frequency of cells in the starting population which grow under the above defined conditions. The frequency is determined by the cell number at which 37% of the wells show no growth. In one study, 1/1500 of the unsorted cells respond while 1/40 of the CD34+ fraction and 1/4000 of the CD34− fraction respond.

The following tables indicate the results for the in vitro culture assays.

TABLE 1

ANTIGEN STAINING PROFILE OF NON-ADHERENT HUMAN CELLS GROWN IN THE CO-CULTURE SYSTEM WITHOUT HYDROCORTISONE

| Sample # | Time in Culture (Weeks) | CD10 (B-cell) | CD19 (B-cell) | CD20 (B-cell) | CD34 (progenitor cell) | CD15 (myeloid) | Methylcellulose (col/$10^5$) |
|---|---|---|---|---|---|---|---|
| S133 | 0 | | | | | | 200 |
| | 7 | 24 | 14 | ND | 38 | ND | |
| | 9 | ND | 7 | 12 | 31 | ND | 92 |
| | 12 | 45 | 29 | 33 | 46 | 45 | 115 |
| | 14 | 21 | 8 | 13 | 18 | 22 | 120 |
| S143 | 0 | | | | | | 156 |
| | 3 | 31 | 18 | 15 | 36 | 40 | 84 |
| | 5 | 39 | 21 | 34 | 65 | 42 | 96 |
| | 8 | 19 | 15 | 45 | 51 | ND | 44 |
| | 10 | 24 | 26 | 19 | 41 | 31 | 140 |

TABLE 2

BONE MARROW UNDER DEXTER CONDITIONS

| Sample # | Time in culture (weeks) | CD15 Condition | CD19 (mono/gran) | CD33 (B-cell) | CD34 myeloid | (progenitor cell) |
|---|---|---|---|---|---|---|
| K146 | 5 | +HC | 93.5 | 0.23 | 40.9 | 20.6 |
| K146 | 9 | +HC | 91.5 | ND | 90.5 | 68.3 |
| K146 | 7/2* | +HC/−HC | 84.6 | 6.0 | ND | 58.4 |
| K146 | 10 | +HC | 95.0 | 0.3 | 26.0 | 23.0 |

*Switch cultures - initiated in hydrocortisone, switched to media without hydrocortisone.

FACS separation of Fetal Bone Marrow (FBM) was performed dividing fractions into $CD34^+$, $10^+$, $19^+$ and $CD34^+10^-$, $19^-$. The fractions are then grown continuously in the absence of hydrocortisone for eight weeks and screened for the presence of myeloid cells and B-cells.

TABLE 3

KINETICS OF B-CELL GENERATION IN VITRO AFTER FACS DEPLETION OF B-CELLS (CD10+, CD19+) FROM FETAL BONE MARROW

| Days in vitro | Cell subset (K336) | CD10 | CD15 | CD19 | k/l | CD33 | CD34 |
|---|---|---|---|---|---|---|---|
| d8 | WBM | 72% | 43% | 65% | 5%/4% | 25% | 4% |
|  | 34+10+19+ | 95 | 14 | 95 | 4/1 | 5 | 4 |
|  | 34+10–19– | 40 | 61 | 32 | 0.1/0.1 | 65 | 6 |
| d15 | WBM | 31 | 34 | 42 | 6/8 | 37 | 3 |
|  | 34+10+19+ | 90 | 6 | 88 | 11/20 | 12 | 1 |
|  | 34+10–19– | 16 | 38 | 18 | 1/2 | 38 | 2 |
| d22 | WBM | 28 | 37 | 21 | 1/3 | 70 | 2 |
|  | 34+10+19+ | 20 | ND* | 20 | 4/12 | ND* | ND* |
|  | 34+10–19– | 31 | 43 | 23 | 1/2 | 73 | 4 |
| d29 | WBM | 49 | 39 | 32 | 1/2 | 54 | 21 |
|  | 34+10+19+ | ND* | ND+ | 15 | 3/9 | 77 | ND* |
|  | 34+10–19– | 73 | 21 | 66 | 1/2 | 31 | 13 |
| d56 | WBM | ND | 19 | 7 | 0/0 | 81 | 3 |
|  | 34+10+19+ | ND | 2 | 0 | 0/0 | 50 | 4 |
|  | 34+10–19– | ND | 15 | 23 | 1/1 | 69 | 2 |

Numbers indicate the percentage of cells stained by the indicated MAb as determined by FACS.
*Indicates insufficient cells for analysis Alternatively, fetal WBM is separated by FACS into $CD34^+$, $33^-$, $10^-$, $19^-$ and the cells are grown in the absence of hydrocortisone. By employing limit dilution about 10–100 cells are found to be able to be maintained in the coculture for greater than six weeks and be differentiated into mature myeloid and B-cells.

the $CD34^+CD10^+CD33^+$ cell subset at time zero. However, at day 21, the $CD34^+CD10^+CD33^+$ and the $CD34^+CD10^-CD33^-$ cell populations have nearly equivalent CFU-GM and BFU-e cell levels. Therefore, the $CD34^+CD10^-CD33^-$ cells have the capacity to give rise to B-cells ($CD19^+$, cytoplasmic $\mu^+$, $sIg^+$), myeloid cells ($CD15^+$–$33^+$, CFU-

TABLE 4

ANALYSIS OF B-LYMPHOID AND MYELOID CELLS IN VITRO CULTURES

| Cells (K283) | Time (days) | % CD10 (Early B-cell) | % CD19 (Pan-B-cell) | % k/l (Mature B) | % CD15 (Myeloid) | % CD34 (Progenitor) | GM Colonies $10^5$ | BFU-e/$10^5$ |
|---|---|---|---|---|---|---|---|---|
| WBM | 0 | 35 | 33 | 7/3 | 45 | 8 | 59 | 89 |
| 34+10+33+ | 0 | 70 | 60 | 2/1 | 35 | 98 | 1199 | 755 |
| 34+10–33– | 0 | 1 | 3 | 0.1/0.1 | 1 | 95 | 72 | 102 |
| WBM | 21 | 25 | 14 | 2.2/1.9 | 20 | 0.13 | 39 | 39 |
| 34+10+33+ | 21 | 12 | 1.7 | 0.2/0.2 | 39 | 1.9 | 1976 | 1576 |
| 34+10–33– | 21 | 52 | 49 | 8.2/4.9 | 31 | 0.4 | 1841 | 1685 |

The results of the CD34, 33, 10 separation are shown in Table 4. The sorted cell populations as well as the unsorted cells were analyzed at the time of separation (t=0) as well as twenty-one days (t=21) later. Analysis of the FACS staining profile at t=0 shows that myeloid and B-cells were effectively removed from the $CD34^+CD10^-CD33^-$ cells with less than 5% contaminating B and myeloid cells. In contrast, by day 21 about 50% of the $CD34^+CD10^-CD33^-$ cells were B-cells. In addition, there was a ten-fold increase in cell numbers between t=0 and t=21. Therefore, there was an overall 100-fold increase in B-cells over the 21 day period. Further, about one-third of the B-cells express sIg with a 2/1 ratio of kappa and lambda light chains. The results indicate that the B-cells are polyclonal and do not represent an Epstein-Barr viral transformation. In comparison, the $CD34^+CD10^+CD33^+$ cells show a dramatic decrease in B-cells and total cell numbers over the 21 day period. The results show that the $CD34^+$ cells which express CD10 and/or CD19 are not long lived progenitors.

Myeloid cell differentiation was analyzed by FACS and methylcellulose assay. FACS analysis shows a 10 fold increase in mature myeloid cells in the $CD34^+CD10^+CD33^+$ cell subset. Analysis of the methylcellulose data showed that 90–95% of the CFU-GM and BFU-e activity is contained in GM) and erythroid cells (BFU-e) over 21 days in culture. Similar results are obtained when cells are separated on the basis of CD34,CD10,CD19,CD33 or CD34,CD3,CD7,CD8, CD10, CD14,CD15,CD19,CD20,CD33.

When $CD34^+$ cells are divided into Thy-$1^+$ and Thy-$1^-$ fractions and assayed in the methylcellulose assay, these two fractions give similar readouts as seen in Table 5. When assayed by limiting dilution and in the cocultures, the $CD34^+$,Thy-$1^+$ fraction is enriched for progenitor activity as evidenced by 1) the percentage of B-cells generated in the coculture; 2) the frequency of responding cells in the limit dilution assay and 3) the frequency of responding cells in the single cell assay (Tables 5 and 6). In order to obtain 75% positive wells in the limit dilution assay, the Thy-$1^+$ fraction required approximately 1/30–1/50 cells whereas the Thy-$1^-$ fraction requires 1/170–1/500 cells. This indicates that the Thy-$1^+$ fraction is further concentrated for the progenitor cell. Moreover, when assayed in the in vivo T-cell assay, the Thy-$1^+$ fraction gives rise to donor derived T-cells, whereas the Thy-$1^-$ fraction does not.

TABLE 5

FREQUENCY ANALYSIS OF CD34+ THY1 POPULATIONS IN METHYCELLULOSE AND LIMIT DILUTION ASSAYS

| Sample | Methycellulose Freq. of GM col | Limit Dilution Frequency 21 days | 28 days | 35 days |
|---|---|---|---|---|
| K275 WBM | 1/10,000 | NA | 1/3000 | NA |
| CD34+Thy+ | 1/284 | " | 1/35 | " |
| CD34+Thy− | 1/312 | " | 1/170 | " |
| K306 WBM | 1/1430 | NA | NA | NA |
| CD34+Thy+ | 1/100 | 1/120 | 1/50 | NA |
| CD34+Thy− | 1/340 | <1/1000 | 1/500 | <1/800 |

TABLE 6

ANALYSIS OF CD34/THY-1 SUBPOPULATIONS IN LONG TERM BULK CULTURES ($10^5$ CELLS/WELL)

| Cell Pop. | Time in Culture | % CD10 (early B-cell) | % CD19 (early B-cell) | % CD15 (myeloid) | % CD33 (myeloid) | CD34 (progenitor cell) |
|---|---|---|---|---|---|---|
| K299 WBM | 8 | 0.1 | 0.1 | 5.4 | 60.8 | 1.0 |
| CD04+Thy1+ | 8 | 31.0 | 37.0 | 42.7 | 20.2 | 0.3 |
| CD34+Thy1− | 8 | 0.5 | 0.4 | 9.0 | 28.1 | 0.4 |
| K332 WBM | 7 | 0.3 | 0.4 | 1.9 | 80.4 | 13.0 |
| CD34+Thy1+ | 7 | 49.0 | 43.4 | 20.0 | 57.7 | 3.5 |
| CD84+Thy1− | 7 | 7.4 | 8.2 | 3.1 | 76.4 | 2.6 |

The thymus assay for T-cell generation was performed as follows. Fetal thymus fragments (individual thymic lobes) are obtained of about 1 mm$^3$ in size. The fragments are cultured in a thymus organ culture system at 25° C. for 3–7 days to stimulate the in vitro receptivity of the thymus for precursor cells.

The cell composition comprising about $10^0$–$10^4$ cells in a FCS containing balanced salt solution is injected at a volume of 1 µl using a glass micropipet linked to an oil-filled micrometric screw-operated syringe. Twenty-four hours after injection, the in vitro colonized thymus fragments are implanted under the kidney capsule of SCID mice. See EPA 0 322 240. The injected cells are HLA mismatched with the thymus. At intervals, recipient animals are sacrificed and the grafts harvested. Cell suspensions are analyzed in a two-color immuno-fluorescence assay for the presence of donor derived T lymphocytes (CD3$^+$, 8$^+$).

TABLE 7

SINGLE CELL PER WELL EXPERIMENTS

| BONE MARROW SUBPOPULATION | FREQUENCY OF GROWTH POSITIVE WELLS | FREQUENCY OF MULTIPOTENT COLONIES |
|---|---|---|
| CD34+Lin+ | 1/80* | 25%** |
| CD34+Lin− | 1/40 | 40 |
| CD34+Thy+ | 1/20 | 75 |
| CD34+Thy− | 1/400 | 0 |
| Thy+Lin+ | 0/854 | 0 |
| Thy+Lin− | 1/21 | 76 |

Single cells with the described phenotype were deposited wells of a 96 well plate which contained a bone marrow stromal cell feeder layer.
*Numbers represent the frequency of cells which gave rise to colonies of >100 cells. The numbers represent the average of at least three separate experiments constituting at least 10 96 well plates.

TABLE 7-continued

SINGLE CELL PER WELL EXPERIMENTS

| BONE MARROW SUBPOPULATION | FREQUENCY OF GROWTH POSITIVE WELLS | FREQUENCY OF MULTIPOTENT COLONIES |
|---|---|---|

**Numbers represent the percentage of colonies arising from single cells which contained cells of the B-lymphoid (CD10+, CD19+), Myeloid (CD15+, CD33+, GM-CFU) and erythroid (BFU-e) lineages simultaneously.

TABLE 8

T-cell repopulation of the human thymus following in vitro colonization by microinjection of leukocyte/precursor cells and regrafting into SCID mice

| Precursor Cell Phenotype | Microinjected Cell Number | Repopulation (+/Total) |
|---|---|---|
| (FBM) CD34$^+$ | $10^4$ | 9/11 |
| (FBM) CD34$^+$ | $10^2$ | 2/4 |
| (FBM) CD34$^+$, 7$^-$ | $10^4$ | 6 wks: 3/5; 11 wks: 2/3 |
| (FBM) CD34$^+$, 7$^+$ | $10^4$ | 6 wks: 3/4; 11 wks: 0/3 |
| (FBM) CD34$^+$, Thy$^+$ | $10^4$ | 16/24 |
| (FBM) CD34$^+$, Thy$^-$ | $10^4$ | 2/24 |
| (HDC) CD34$^+$ | $2 \times 10^3$ | 2/5 |
| (FL) HLA-DR$^+$, Lin*$^-$ | $10^4$ | 11/14 |

FBM: Fetal Bone Marrow
Lin* CD3, -8, -10, -15, -19, -20
HDC: Human coculture cells grown under Dexter-like conditions for 6 weeks.
FL: Fetal Liver The above results show that a small population of selected cells give rise to T-cells, resulting in terminally differentiated CD4$^+$ and CD8$^+$ T-cells. The Thy-1$^-$ population does not appear to provide a detectable level of differentiated T-cells.

Human bone fragments can be transplanted at various sites (i.p., s.c., etc.) into either irradiated (200–300 rad) or non-irradiated CB17 SCID/SCID mice. The bone fragments grow for periods of at least 9 months with the continuous production of human B, myeloid and erythroid cells. The bone fragments act as a supportive microenvironment for human allogeneic progenitor populations. Allogeneic bone marrow progenitors (mismatch for HLA Class I) may be injected into the bone fragment either before or after transplantation into the recipient mouse. If the progenitor cells are to be injected before transplantation, the sorted cells are microinjected into the bone after which the injected bones are incubated overnight at room temperature before transplantation into the CB17 SCID/SCID mice (i.p. or s.c.). If progenitor cells are to be microinjected after transplantation, CB17 SCID/SCID mice are transplanted (i.p., s.c.) with bone fragments. After 6 weeks, the bone graft can be irradiated (200–1000 rads to the graft with shielding of the mouse) followed by injection of progenitor cells. Alternatively, the progenitor cells may be injected into non-irradiated bone fragments.

Results with the bone marrow assay indicate that CD34+ cells contain virtually all of the bone marrow regenerating capacity. The bone marrow regenerating capacity. Subfractionation of the CD34 population has shown that the Thy+ cells in the CD34 subset (5% of CD34 cells) contain virtually all of the B-cell, myeloid cell and erythroid progenitor activity in the CD34 fraction. The assay may be successfully performed with between 10 and 10,000 cells. A summary is shown in Table 9.

addition, the cells may be modified by appropriate recombination, either homologous or non-homologous, to correct genetic defects or provide genetic capabilities naturally lacking in the stem cells, either as to the individual or as to stem cells generally. In addition, because the composition is substantially free of other cells, the stem cell composition may be used to isolate and define factors associated with regeneration and differentiation.

All publications and patent applications mentioned in this specification are indicative of the level of skill of those skilled in the art to which this invention pertains. All publications and patent applications are herein incorporated by reference to the same extent as if each individual publication or patent application was specifically and individually indicated to be incorporated by reference.

TABLE 9

COMPARISON OF THE DIFFERENTIATION POTENTIAL OF HUMAN PROGENITOR POPULATIONS

| BONE MARROW SUBPOPULATION | METHYLCELLULOSE GM COLONY FREQUENCY | CO-CULTURE COLONY FREQUENCY | T-CELL PROGENITOR ASSAY | BONE MARROW TRANSPLANT ASSAY |
|---|---|---|---|---|
| WHOLE BM | 1/5,000 | 1/3000 | ++ | ++ |
| CD34+(2-10%)* | 1/500 | 1/200 | ++ | ++ |
| CD34-(90-98%) | 1/50,000 | 1/50,000 | +/- | +/- |
| CD34+Thy+ (0.1-0.5%) | 1/300 | 1/20 | +++ | +++ |
| CD34+Thy- (2-10%) | 1/300 | 1/400 | +/- | - |
| Thy+Lin+ ((0.3-2.0%) | 1/1000 | 0/854 | ** | ** |
| Thy+Lin- (0.1-0.5%) | 1/500 | 1/21 | ** | ** |

*Percentage represents the percentage of whole bone marrow with the designated phenotype.
** Experiments underway.

A secondary transfer assay may be used to evaluate self-renewal and longevity of human stem cells. Donor progenitor cells are injected into HLA mismatched bone fragments as above. After 2 to 3 months, the resulting donor cells which have expanded can be resorted for the "stem cell" phenotype (CD34+, Thy+, Lin−). These cells are then reinjected into a second HLA mismatched donor. After 1 to 3 months, the bone is evaluated for various progenitor populations as well as stem cells. In this way, one can evaluate the long-term potential of "stem cells" to give rise to hematopoietic cells of various lineages as well as the number of "stem cells" which arise from a known input "stem cell" number. This provides an estimate of stem cell self-renewal. In the subject assay, the stem cells of the subject invention would provide long-term renewal.

It is evident from the above results, that the subject invention provides for cells which are substantially homogenous in the characteristics of human hematopoietic stem cells in accordance with this invention. Thus, by appropriate selection with particular factors and the development of bioassays which allow for self regeneration of stem cells and screening of the stem cells as to their surface markers, a substantially homogenous viable human hematopoietic stem cell composition may be produced for a variety of purposes. The stem cells may be used in bone marrow transplants, where the cells may be freed of neoplastic cells or other cells that are pathogenic, e.g., HIV-infected cells. Further, the use of pure stem cells will preclude graft-versus-host disease. In The invention now being fully described, it will be apparent to one of ordinary skill in the art that many changes and modifications can be made thereto without departing from the spirit or scope of the appended claims.

What is claimed is:

1. A method for identifying the presence of a growth factor that affects the self-regeneration of human hematopoietic stem cells, said method comprising:

combining a composition suspected of containing at least one growth factor that affects the self-regeneration of human hematopoietic stem cells with a composition comprising human hematopoietic stem cells and having fewer than 5% lineage committed cells, wherein said human hematopoietic stem cells are characterized as Thy-1+, capable of self regeneration, and differentiation to members of the lymphoid, erythroid and myelomonocytic lineages; and determining the self-regeneration of said stem cells as a function of the presence of at least one of said growth factors in said composition, wherein said stem cell self-regeneration is indicative of the presence of a growth factor that affects the self-regeneration of human hematopoietic stem cells in said composition.

2. A method according to claim 1, wherein said human hematopoietic stem cells are further characterized by being CD34+ and lin−.

* * * * *